United States Patent [19]

Senda et al.

[11] Patent Number: 4,835,292

[45] Date of Patent: May 30, 1989

[54] NOVEL OPTICALLY ACTIVE ALCOHOL

[75] Inventors: Shuji Senda; Yutaka Nakazono, both of Osaka; Kenji Mori, Tokyo, all of Japan

[73] Assignee: Nitto Electric Industrial, Osaka, Japan

[21] Appl. No.: 23,751

[22] Filed: Mar. 9, 1987

[30] Foreign Application Priority Data

Jul. 11, 1986 [JP] Japan .................................. 61-164416

[51] Int. Cl.$^4$ ........................................... C07D 309/12
[52] U.S. Cl. ................................ 549/423; 549/273
[58] Field of Search ......................................... 549/423

[56] References Cited

PUBLICATIONS

Mori et al., Tet., 42(23), 6459 (1986).
Organic Chemistry, Pine et al., McGraw-Hill Int'l Book Co., pp. 118–119.
Rocca et al., "The Queen Recognition . . . (E)-6-(-1-Pentenyl)-2H-Pyran-2-One", Tetrahedron Letters, vol. 24, No. 18, pp. 1889–1892, (1983).
Mori & Nakazono, "Synthesis of Both the Enantiomers . . . Fire Ant", Tetrahedron Letters, vol. 42, No. 23, pp. 6459–6464, (1986).
Senda & Mori, "Synthesis of (-)-Invictolide, . . . Fire Ant", Agric. Biol. Chem., 51, (5), 1379–1384, (1987).
Ann. Entomol. Soc. Am., 73 (5), 609–612 (1980) R. K. Vander Meer et al.
Tetrahedron Letters, 24(18), 1882–1892(1983) J. R. Rocca et al.

*Primary Examiner*—Nicky Chan
*Attorney, Agent, or Firm*—Sughrue, Mion, Zinn, Macpeak & Seas

[57] ABSTRACT (2R,3S,4R)-(+)- and (2S,3R,4S)-(-)-2,4-dimethyl-3-tetrahydropyranyloxy-1-heptanols which are important intermediates for synthesis of invictolide, one component of a queen recognition peromone of red imported fire ant.

3 Claims, 9 Drawing Sheets

NOVEL OPTICALLY ACTIVE ALCOHOL

FIELD OF THE INVENTION

This invention relates to novel optically active alcohols, and more specifically (2R,3S,4R)-(+)- and (2S,3R,4S)-(−)-2,4-dimethyl-3-tetrahydropyranyloxy-1-heptanols which are important intermediates for synthesis of invictolide, one component of a queen recognition pheromone of red imported fire ant (*Solenopsis invicta*).

BACKGROUND OF THE INVENTION

Red imported fire ant is an insect pest which particularly causes enormous damage to agricultural crops in U.S.A. As the use of agricultural chemicals has been restricted or even prohibited in recent years, it has been strongly desired to develop a new method of controlling this insect.

Controlling methods using various biologically active substances have been studied, and the use of pheromones has especially attracted attention. In particular, since the queen recognition pheromone is a pheromone by whick worker ants recognize the queen, the use of such a queen recognition pheromone will permit an effective control of this insect species.

The queen recognition pheromone is composed mainly of the following three components.

The compound (b) which is called invictolide is very difficult to synthesize stereoselectively since it contains four asymmetric carbons. The only prior report on its synthesis is Zeigler et al., *Tetrahedron*, 27, 1229 (1986). However, this prior method of synthesis requires a number of steps and is difficult to employ industrially. Moreover, the invictolide obtained by this method has a low optical purity.

SUMMARY OF THE INVENTION

As a result of extensive investigations to establish a simple industrial process for producing optically active invictolide, the present inventors succeeded to obtain novel optically active alcohols in accordance with this invention as a starting material for the stereoselective synthesis of invictolide. They have also found that by using these novel optically active alcohols, optically active invictolide having a high optical purity can be easily produced by less process steps.

Accordingly, an object of this invention is to provide a novel optically active alcohol, particularly optically active 2,4-dimethyl-3-tetrahydropyranyloxy-1-heptanol which is useful as a starting material for easily producing optically active invictolide having a high optical purity.

The novel optically active alcohol in accordance with this invention is represented by the following structural formula wherein the configuration of the 2,3 and 4 positions is either (2R,3S,4R) or (2S,3R,4S).

Specifically, the present invention provides (2R,3S,4R)-(+)-2,4-dimethyl-2-tetrahydropyranyloxy-1-heptanol represented by structural formula (Ia), and (2S,3R,4S)-(−)-2,4-dimethyl-3-tetrahydropyranyloxy-1-heptanol represented by structural formula (Ib) as the novel optically active alcohol.

DETAILED DESCRIPTION OF THE INVENTION

The optically active alcohol of this invention can be obtained from an optically active epoxide (2) in accordance with the following scheme (K. Mori et al., *Tetrahedron*, 36, 2209 (1980)).

The epoxide (2) is first ring-opened with a cyanide ion and treated with an acid to form a hydroxy acid. it is methyl-esterified to obtain the hydroxy ester (3). The ester is reacted with methyl iodide in the presence of a base to obtain the α-methylhydroxy ester (4). Thereafter, the hydroxyl group of this compound is protected with a tetrahydropyranyl group, and then the ester is reduced to an alcohol. As a result, the optically active alcohol (1) can be obtained.

The production of the optically active alcohol of this invention will be described below in detail.

The optically active epoxide (2) can be obtained from the optically active amino acid (5), for example, in accordance with the method described in the above-described literature reference.

Likewise, (+)-(2) can be obtained from (−)-(5).

To ring-open the epoxide (2), the epoxide (2) is reacted with 1 to 10 equivalents, preferably 1.2 to 5 equivalents, based on the epoxide (2), of an alkali cyanide such as sodium cyanide or potassium cyanide in a solvent. There is no restriction on this solvent so long as it dissolves the epoxide (2) and the alkali cyanide used and does not inhibit the ring-opening reaction of the epoxide by the cyanide ion. Preferably, it is a lower aliphatic alcohol such as methanol or ethanol, or its aqueous solution. The reaction temperature is from room temperature to the boiling point of the solvent used, preferably from 50° C. to the boiling point of the solvent. After the reaction, the reaction solution is concentrated and treated with an acid to obtain the hydroxycarboxylic acid. Methyl-esterification of the hydroxycarboxylic acid in a conventional manner gives the hydroxy ester (3).

The methyl group can be stereoselectively introduced into the α-carbon of the hydroxy ester (3) by the method of Fráter (G. Fráter, *Helv.*, 62, 6829 (1979)). For example, the hydroxy ester (3) is reacted with at least 2 equivalents, preferably 2 to 4 equivalents, of lithium diisopropylamide in a solvent, preferably at a low temperature of 0° C. or less, and then reacted with methyl iodide. In this reaction, the solvent is not particularly limited so long as it does not deleteriously affect the reaction. Usually, dry tetrahydrofuran is suitably used. The amount of methyl iodide used is at least 1 equivalent, preferably 1 to 3 equivalents, to the hydroxy ester. Preferably, the reaction is carried out at a temperature of 0° C. or less. The reaction is stopped in a conventional manner, and then α-methylhydroxy ester (4) as the reaction product is isolated by, for example, chromatography or distillation.

The hydroxyl group of the resulting α-methylhydroxy ester is protected with a tetrahydropyranyl group in a conventional manner. Methods of protecting the hydroxyl group with the tetrahydropyranyl group are well known. For example, as described in T. W. Green, *Protective Groups in Organic Synthesis*, John Wiley & Sons, 1981, the protection is effected by reacting the hydroxy ester (4) with dihydropyran in the presence of a catalytic amount of p-toluenesulfonic acid.

Thereafter, the tetrahydropyranyloxy hydroxy ester is reduced with a reducing agent such as lithium aluminum hydride in a solvent to give the optically active alcohol (1) of this invention. The amount of lithium aluminum hydride used is 0.5 to 5 equivalents, preferably 0.8 to 2 equivalents, to the tetrahydropyranyloxyhydroxy ester. The solvent is preferably ether.

The optically active alcohol of the invention can be converted to invictolide in accordance with the following scheme.

Ts = p-toluenesulfonyl group;

THP =

Specifically, the optically active alcohol (1) is tosylated and then iodinated. The product is subjected to asymmetric alkylation using propionamide of prolinol in accordance with the method of Evans et al. (*Tetrahedron Letters*, 24, 4233 (1980)), and then treated with an acid. As a result, elimination of the protective group, elimination of prolinol and lactonization take place, and invictolide can be obtained.

By using the optically active alcohol of the invention as a starting material, optically active invictolide having a high optical purity can be obtained by a smaller number of process steps.

The following examples illustrate the present invention more specifically.

Synthesis of methyl (+)-3-hydroxy-4-methylheptanoate (+)-(3)

720 mg (5.71 mmol) of (−)-epoxide (2) and 840 mg (17.1 mmol) of sodium cyanide were dissolved in 10 ml of a 40% aqueous solution of ethanol, and the solution was refluxed for 6 hours. Then, ethanol was evaporated under reduced pressure. The aqueous layer was washed with ether, and 2N hydrochloric acid was added to the aqueous layer to adjust its pH to 3.5. The aqueous layer was then extracted with methylene chloride, dried over anhydrous sodium sulfate, filtered and concentrated to give 0.90 g of crude 3-hydroxy-4-methyl-heptanoic acid.

The crude product was treated with diazomethane, and distilled to give 560 mg (yield 56.3%) of methyl (+)-3-hydroxy-4-methylheptanoate.

Synthesis of methyl (−)-3-hydroxy-4-methylheptanoate (−)-(3)

Methyl (−)-3-hydroxy-4-methylheptanoate (3) was produced in a yield of 36% by operating in the same way as above except that (+)-epoxide (2) was used instead of (−)-epoxide (2).

Synthesis of methyl (+)-3-hydroxy-2,4-dimethylheptanoate (+)-(4)

In 40 ml of dry tetrahydrofuran, 1.31 g (12.9 mmol) of diisopropylamine was reacted with 5.22 ml (1.65N hexane solution, 8.61 mmol) of n-butyllithium at a temperature of −15° C. for 20 minutes to prepare a lithium diisopropylamide solution.

A solution of 500 mg (2.87 mmol) of methyl (+)-3-hydroxy-4-methylheptanoate (+)-(3) in 5 ml of dry tetrahydrofuran was added dropwise to the above lithium diisopropylamide solution at −65° C. over 1 minute in an atmosphere of nitrogen, and the mixture was maintained at −15° C. for 35 minutes. Then, 2.25 ml (12.9 mmol) of hexamethylphosphoric triamide was added, and the temperature of the mixture was again adjusted to −65° C.

A solution of 1,027 mg (7.23 mmol) of methyl iodide in 5 ml of dry tetrahydrofuran was added dropwise at −65° C. for 2 minutes. The mixture was maintained at −65° C. for 4 hours, and then at −40° C. for 1 day, and further left to stand at −20° C. for 3 days. Thereafter, a saturated aqueous solution of ammonium chloride was added to stop the reaction. The reaction mixture was extracted with ether. The ethereal solution was washed with an aqueous solution of sodium chloride, dried over anhydrous magnesium sulfate, filtered, concentrated, and distilled to give 352 mg (yield 65.1%) of methyl (+)-3-hydroxy-2,4-dimethylhaptanoate (+)-(4).

Figure 1:
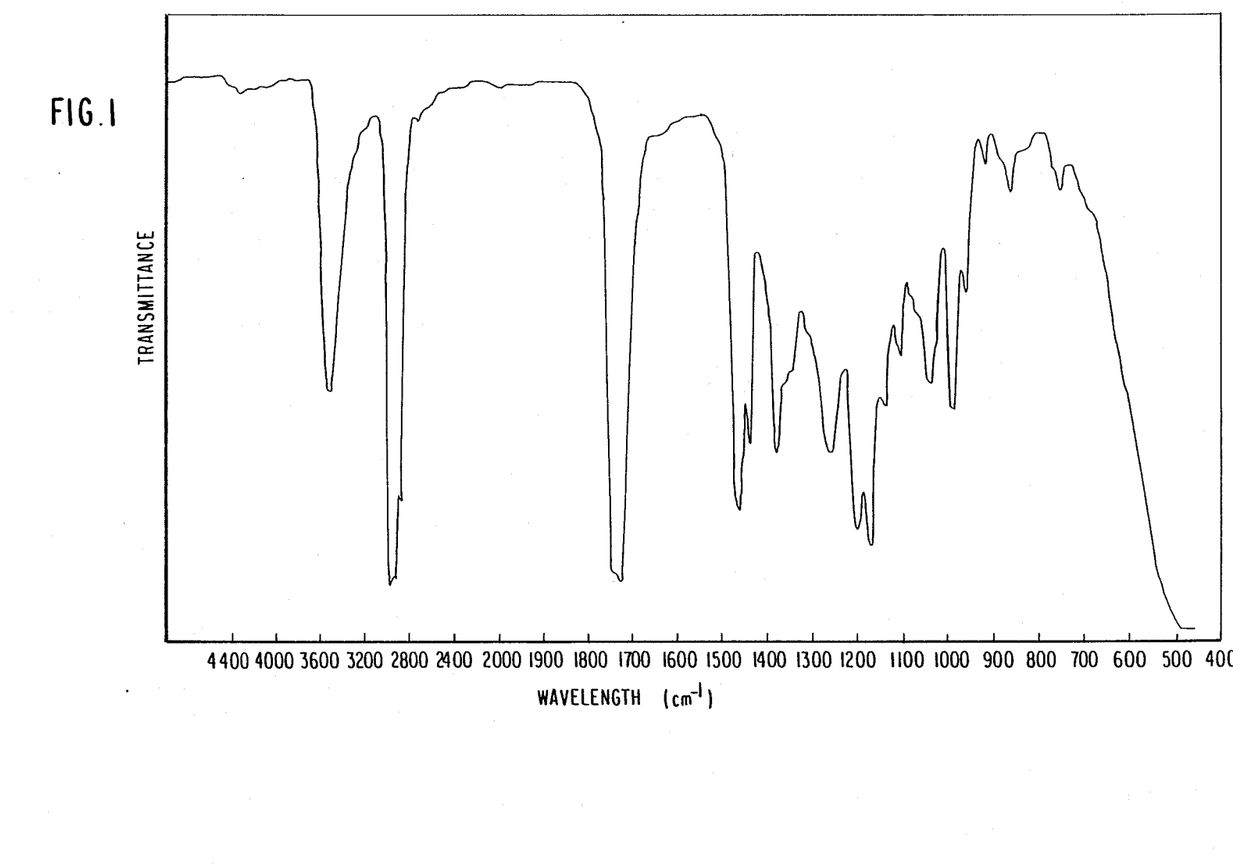
FIGS. 1, 2 and 3 are respectively the infrared absorption spectrum, proton nuclear magnetic resonance spectrum and $^{13}$C nuclear magnetic resonance spectrum of methyl (2S,3S,4R)-(+)-2,4-dimethyl-3-heptanoate.
Figure 2:
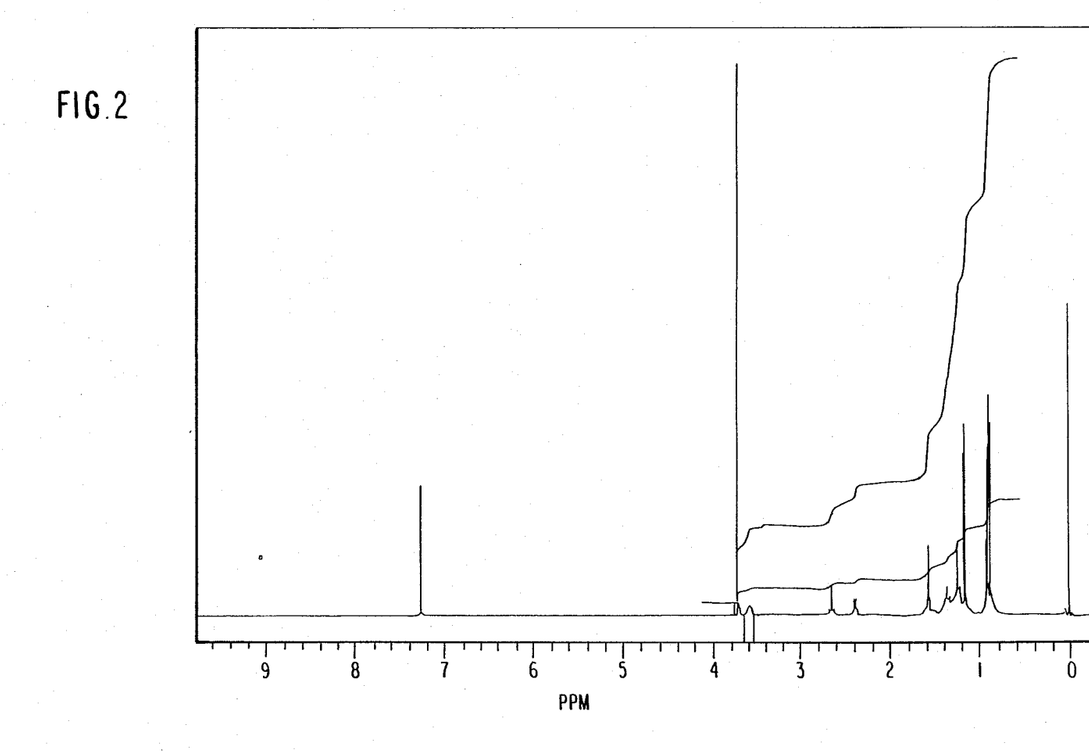
Figure 3:
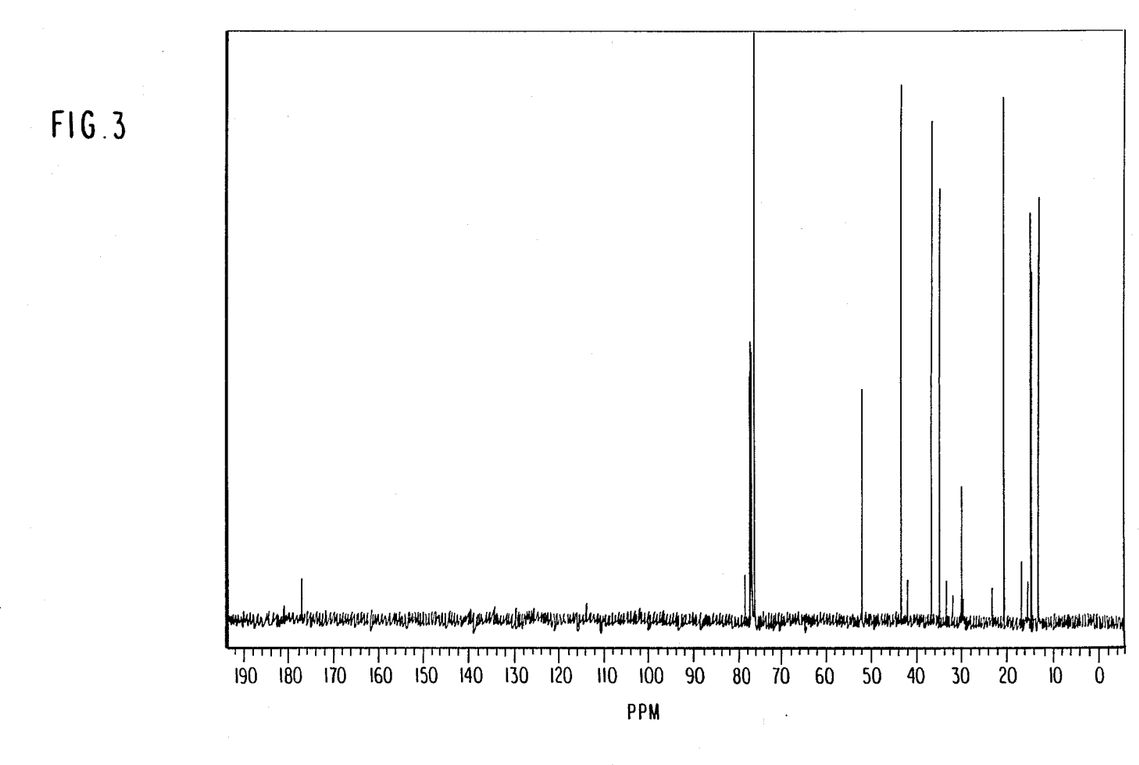

The infrared absorption spectrum, proton nuclear magnetic resonance spectrum and $^{13}C$ nuclear magnetic resonance spectrum of methyl (+)-3-hydroxy-2,4-dimethylhaptanoate (+)-(4) are shown respectively in FIGS. 1, 2 and 3.

Boiling point: 75°–78° C./1.5 mm Hg

| Elemental analysis ($C_{10}H_{20}O_3$): | | |
|---|---|---|
| | C | H |
| Found: | 63.52 | 10.88 |
| Calculated: | 63.79 | 10.71 |

IR absorption spectrum (neat): 3,520 (m), 2,960 (s), 2,930 (s), 2,880 (m), 1,725 (s), 1,460 (s), 1,435 (m), 1,380 (m), 1,260 (m), 1,200 (s), 1,170 (s), 1,140 (m), 1,105 (m), 1,030 (m), 980 (m), 955 (m), 915 (w), 855 (w), 740 (w)

$^1$H-NMR spectrum (400 MHz, CDCl$_3$): 0.872 (3H, d, J=6.8 Hz), 0.904 (3H, t, J=7 Hz), 1.161 (3H, d, J=7.32 Hz), 1.18–1.43 (5H, m), 2.396 (1H, brd, J=6.4 Hz), 2.647 (1H, dq, J=7 Hz, J=7 Hz), 3.55–3.63 (1H, m), 3.714 (3H, s)

$^{13}$C-NMR spectrum (100 MHz, CDCl$_3$): 12.774, 14.243, 14.468, 20.296, 34.762, 36.213, 43.091, 51.772, 76.067, 176.980 $[\alpha]_D^{26}$: +13.5° (c=0.555, CHCl$_3$)

Synthesis of methyl (−)-3-hydroxy-2,4-dimethylheptanoate (4)

Methyl (−)-3-hydroxy-2,4-dimethylheptanoate (−)-(4) was produced in a yield of 57% by operating in the same way as above except that methyl (−)-3-hydroxy-4-methylheptanoate (−)-(3) was used instead of methyl (+)-3-hydroxy-4-methylheptanoate.

Figure 4:
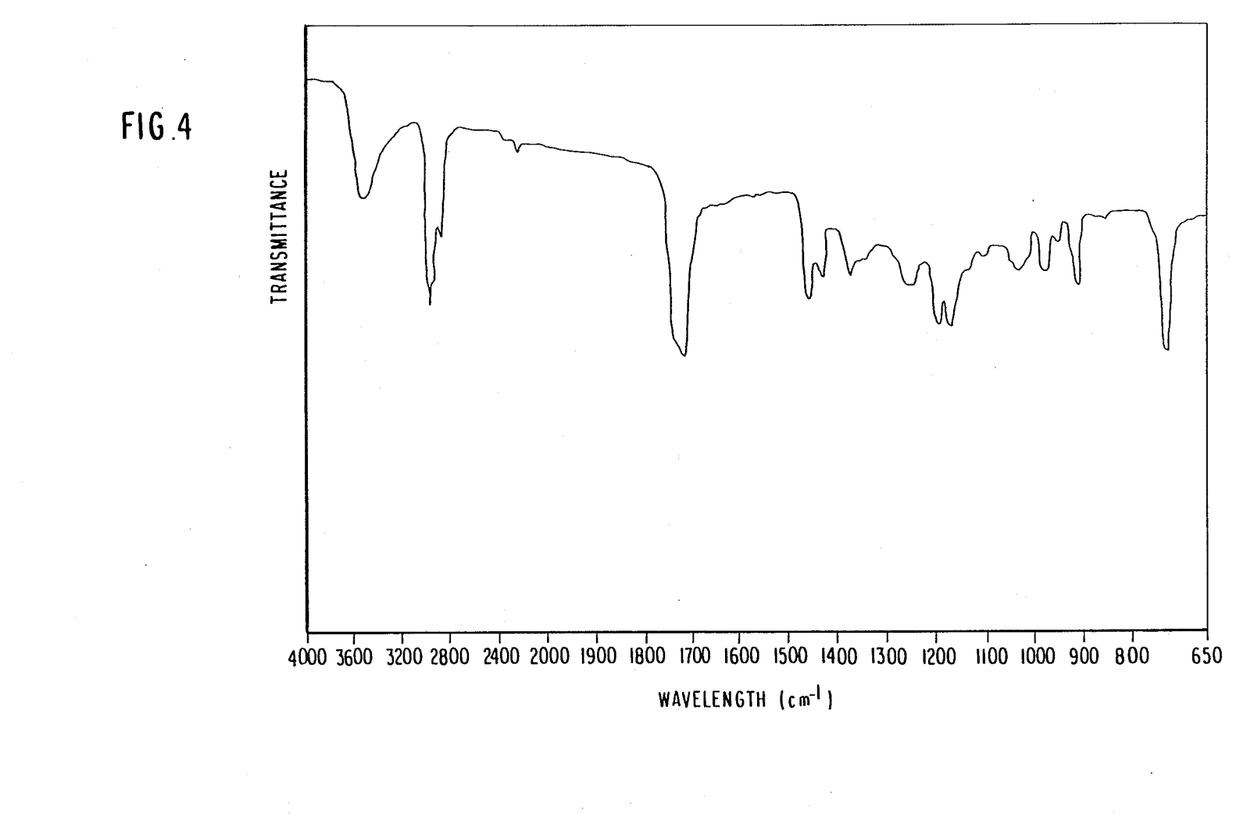
FIGS. 4 and 5 are respectively the infrared absorption spectrum and proton nuclear magnetic resonance spectrum of methyl (2R,3R,4S)-(−)-2,4-dimethyl-3-heptanoate.
Figure 5:
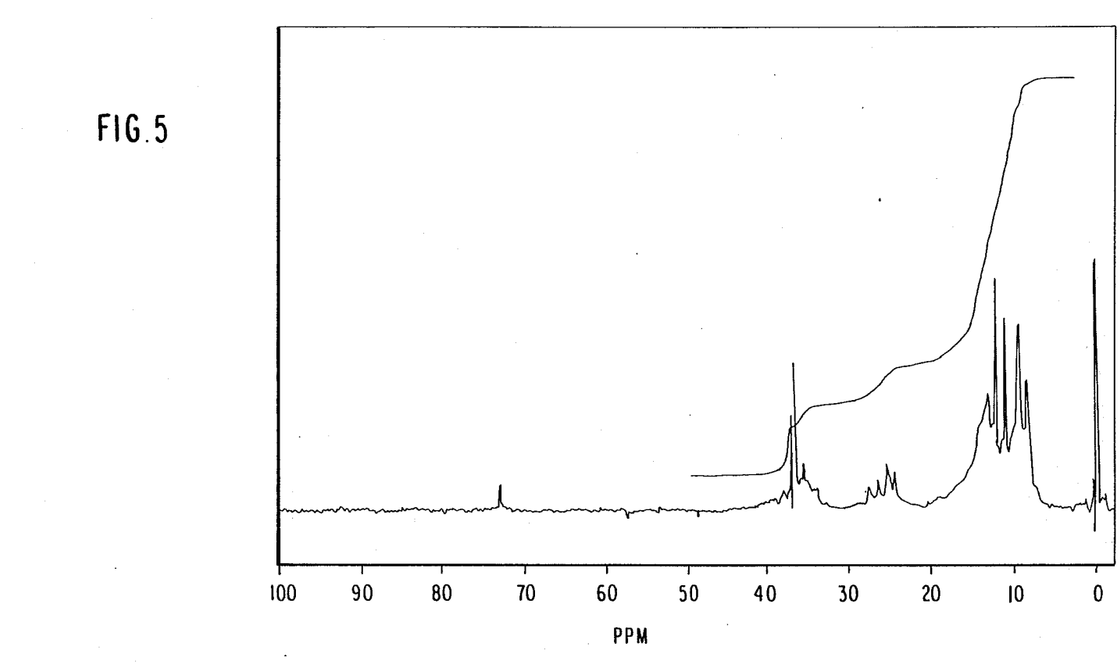

The infrared absorption spectrum and proton nuclear magnetic resonance spectrum of methyl (−)-3-hydroxy-2,4-dimethylheptanoate (−)-(4) are shown respectively in FIGS. 4 and 5.

Boiling point: 75° C./1.5 mm Hg $[\alpha]_D^{23}$: −15.1° (c=0.470, CHCl$_3$)

| Elemental analysis ($C_{10}H_{20}O_3$): | | |
| --- | --- | --- |
| | C | H |
| Found: | 63.51 | 10.68 |
| Calculated: | 63.79 | 10.71 |

Synthesis of (+)-2,4-dimethyl-3-tetrahydropyranyloxy-1-heptanol (Ia)

200 mg (1.06 mmol) of methyl (+)-3-hydroxy-2,4-dimethylheptanoate (+)-(4) was dissolved in 4 ml of tetrahydrofuran, and 134 mg (1.59 mmol) of dihydropyran and 1 mg of pyridinium p-toluenesulfonate were added, and the mixture was reacted overnight at room temperature. Since TLC (Thin Layer Chromatography) showed that the starting materials still remained, 5 mg of pyridinium p-toluenesulfonate and 3 ml of methylene chloride were added, and the reaction was further carried out overnight at room temperature. The reaction mixture was extracted with ether. The ethereal layer was washed with a saturated aqueous solution of sodium hydrogencarbonate and then with an aqueous solution of sodium chloride, and dried over anhydrous sodium sulfate, filtered, and concentrated to give 350 mg of crude methyl (+)-2,4-dimethyl-3-tetrahydropyranyloxy-1-heptanoate.

The crude reaction product (350 mg) was dissolved in 35 ml of ether, and under ice cooling, 80 mg (2.12 mmol) of lithium aluminum hydride was added. The mixture was maintained at room temperature for 3 hours, and 0.1 ml of water, a 10% aqueous solution of sodium hydroxide and then 0.3 ml of water were added to the reaction mixture. The precipitate was separated by filtration, concentrated and purified by chromatography (Wako Gel C-200 (10 g), hexane/ether) to give 260 mg (yield 96.9%) of (+)-2,4-dimethyl-3-tetrahydropyranyloxy-1-heptanol (Ia).

Figure 6:
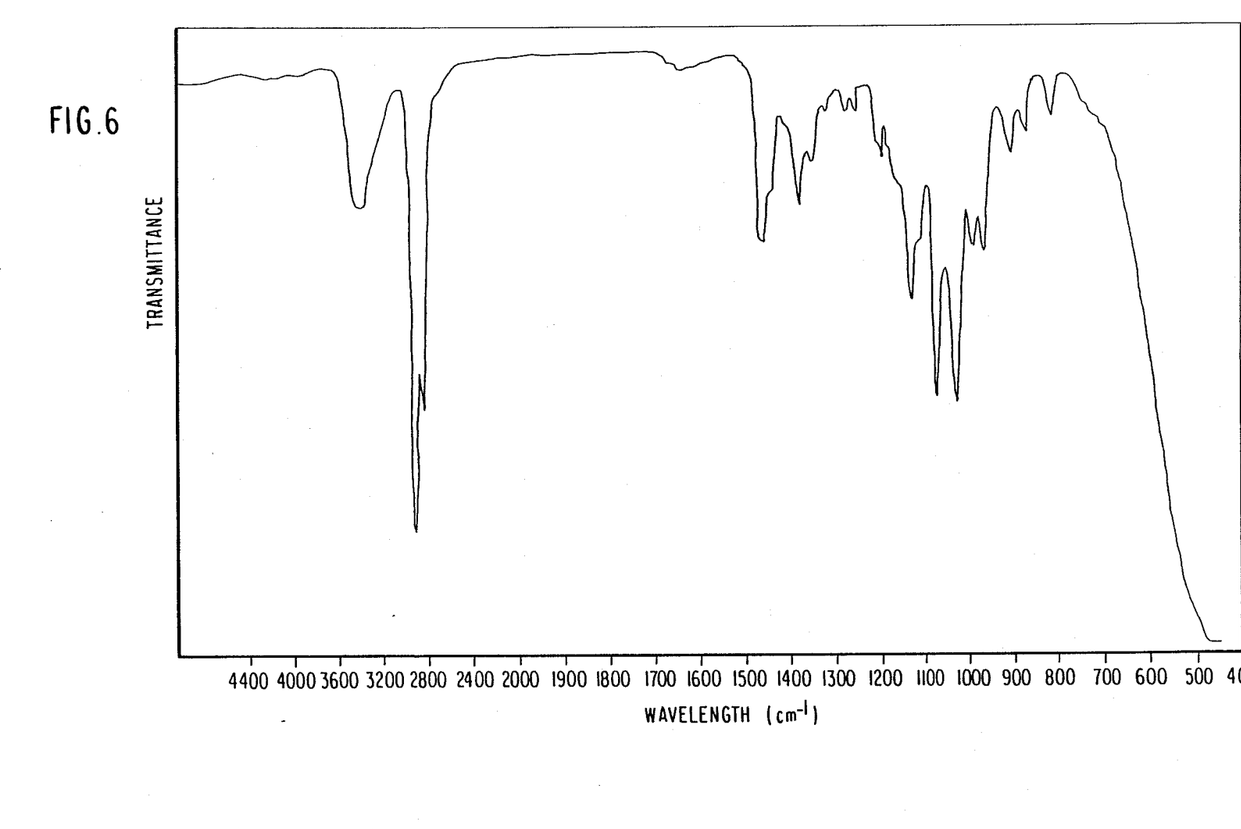
FIGS. 6 and 7 are respectively the infrared absorption spectrum and photon nuclear magnetic resonance spectrum of (+)-2,4-dimethyl-3-tetrahydropyranyloxy-1-heptanol.
Figure 7:
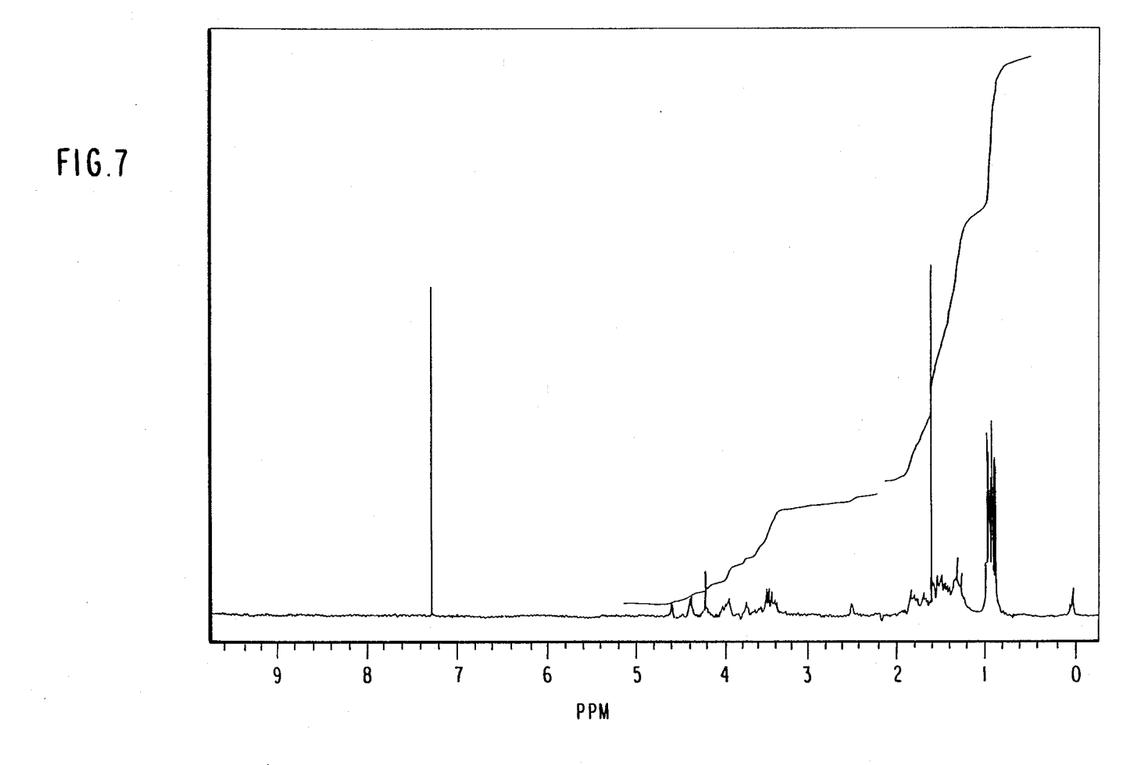

The infrared absorption spectrum and proton nuclear magnetic resonance spectrum of the product (Ia) are shown respectively in FIGS. 6 and 7.

| Elemental analysis ($C_{14}H_{28}O_3$): | | |
| --- | --- | --- |
| | C | H |
| Found: | 68.85 | 11.40 |
| Calculated: | 68.81 | 11.55 |

IR absorption spectrum (neat): 3,420 (m), 2,920 (s), 2,850 (s), 1,450 (m), 1,380 (m), 1,350 (w), 1,320 (w), 1,275 (w), 1,250 (w), 1,200 (w), 1,130 (s), 1,070 (s), 1,025 (s), 990 (m), 965 (m), 900 (w), 865 (w), 805 (w)

$^1$H-NMR spectrum (400 MHz, $CDCl_3$): 0.86–1.01 (9H, m), 1.18–1.88 (12H, m), 3.35–4.65 (7H, m) $[\alpha]_D^{20}$: +13.6° (c=1.06, $CHCl_3$)

Synthesis of (−)-2,4-dimethyl-3-tetrahydropyranyloxy-1-heptanol (Ib)

(−)-2,4-Dimethyl-3-tetrahydropyranyloxy-1-heptanol (Ib) was produced in a yield of 99% by operating in the same way as above except that methyl (−)-3-hydroxy-2,4-dimethylheptanoate (−)-(4) was used instead of (+)-3-hydroxy-2,4-dimethylheptanoate (+)-(4).

Figure 8:
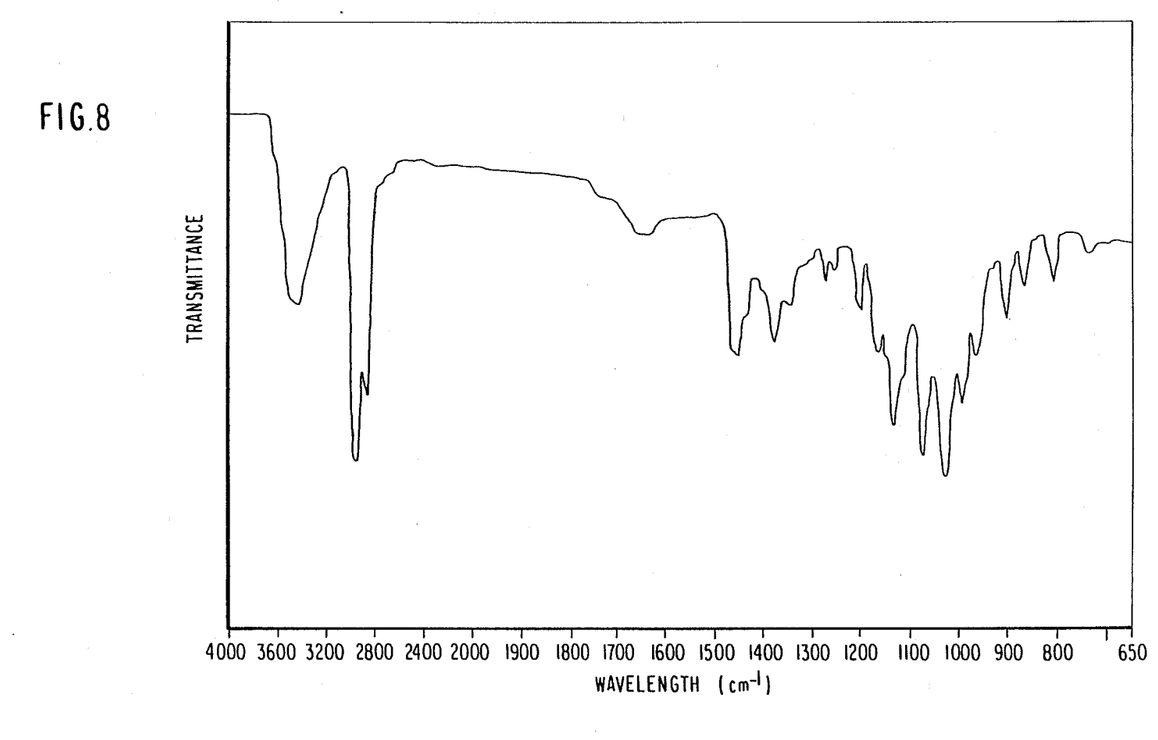
FIGS. 8 and 9 are respectively the infrared absorption spectrum and proton nuclear magnetic resonance spectrum of (−)-2,4-dimethyl-3-tetrahydropyranyloxy-1-heptanol.
Figure 9:
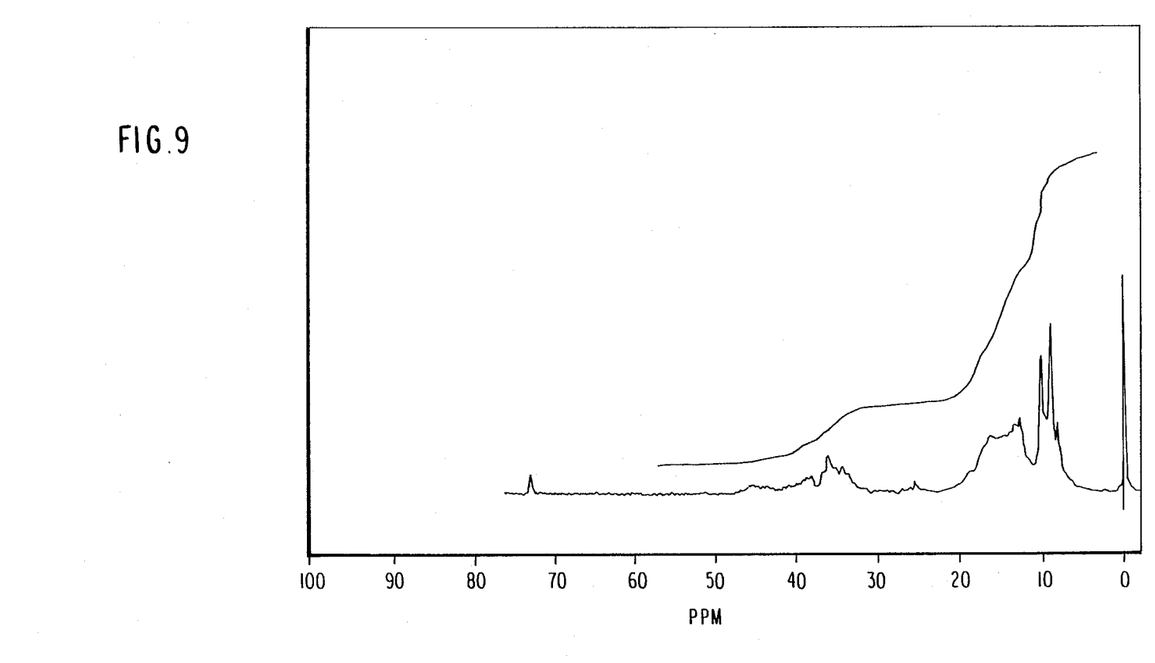

The infrared absorption spectrum and proton nuclear magnetic resonance spectrum of the product (Ib) are shown respectively in FIGS. 8 and 9.

| Elemental analysis ($C_{24}H_{28}O_3$): | | |
| --- | --- | --- |
| | C | H |
| Found: | 68.92 | 11.50 |
| Calculated: | 68.81 | 11.55 |

$[\alpha]_D^{20}$: −13.8° (c=1.00, $CHCl_3$)

An example of synthesis of invictolide is shown below.

Synthesis of 2,4-dimethyl-1-iodo-3-tetrahydropyranyloxy-heptane (8)

230 mg (0.93 mmol) of the above compound (Ia) was dissolved in 2 ml of pyridine, and under ice cooling, 270 mg (1.41 mmol) of p-toluenesulfonyl chloride was added. Under ice cooling, the mixture was reacted for 3 hours, and then left to stand overnight at 3° C. The reaction mixture was put in water and extracted with ether. The ethereal layer was washed with 1N hydrochloric acid, a saturated aqueous solution of copper sulfate, water, a saturated aqueous solution of sodium hydrogencarbonate and an aqueous solution of sodium chloride in this sequence, dried over anhydrous sodium sulfate, filtered and concentrated to obtain 330 mg of a crude tosylate (7).

The crude tosylate (7) (330 mg) was dissolved in 3 ml of dry dimethylformamide, and 170 mg (2 mmol) of sodium hydrogencarbonate and 212 mg (1.41 mmol) of sodium iodide were added to the solution. The mixture was reacted at room temperature for 3 days and further at 50° to 60° C. for 1 day. The reaction mixture was then put into water and extracted with benzene. The benzene layer was washed with an aqueous solution of sodium chloride, dried over anhydrous sodium sulfate, filtered, concentrated, and purified by chromatography (Wako Gel C-200 (10 g), hexane/ether) to give 170 mg (yield from (7) 50.9%) of 2,4-dimethyl-1-iodo-3-tetrahydropyranyloxy-heptane (8).

Synthesis of 1-(5'-tetrahydropyranyloxy-2',4',6'-trimethylnonanoyl)-2-hydroxymethylpyrrolidine (9)

199 mg (1.97 mmol) of diisopropylamine was dissolved in 2.5 ml of dry tetrahydrofuran, and in an atmosphere of nitrogen, 0.795 ml of n-butyllithium (1.65N hexane solution) was added dropwise at 1° C., and the mixture was maintained at 1° C. for 45 minutes. To the reaction mixture were added dropwise at 1° C. 68.7 mg (0.438 mmol) of (S)-(−)-prolinol propionamide and 0.5 ml of dry tetrahydrofuran, and the mixture was reacted at room temperature for 1 hour. To the reaction mixture was added dropwise 0.2 ml (1.15 mmol) of dry HMPA, and the mixture was cooled to −100° C. Then, 112 mg (0.29 mmol) of the compound (8) was dissolved in 0.5 ml of dry tetrahydrofuran, and reacted at −100° C. for 11 hours, and left to stand at −80° C. for 4 days. Water was added to the reaction mixture, and the mixture was extracted with ether. The ethereal layer was washed with 1N hydrochloric acid and an aqueous solution of sodium chloride, dried over anhydrous magnesium sulfate, filtered, concentrated, and purified by chromatography (Wako Gel C-200 (3 g), hexane/ether/methanol) to give 97.0 mg (yield 86.6%) of compound (9).

Synthesis of (−)-invictolide (b)

90 mg (0.234 mmol) of the compound (9) and 1N hydrochloric acid were mixed and refluxed for 2 hours. Chloroform was added, and the mixture was stirred at room temperature for 1 hour. The chloroform layer was separated, and the aqueous layer was further extracted with chloroform. All chloroform layers were collected, dried over anhydrous magnesium sulfate, filtered, concentrated, and purified by chromatography (Wako Gel C-200 (2 g), hexane/ether) to give 27.7 mg (yield 59.8%) of (−)-b.

| Elemental analysis ($C_{12}H_{22}O_2$): | | |
|---|---|---|
| | C | H |
| Found: | 72.47 | 11.35 |
| Calculated: | 72.68 | 11.18 |

IR absorption spectrum (neat): 2,960 (s), 2,930 (s), 2,870 (m), 1,740 (s), 1,460 (m), 1,380 (m), 1,330 (w), 1,235 (m), 1,195 (s), 1,150 (m), 1,120 (m), 1,090 (m), 1,020 (m), 990 (m), 720 (w)

$^1$H-NMR spectrum (400 MHz, CDCl$_3$): 0.903 (3H, t, J=7.5 Hz), 0.914 (3H, d, J=6.8 Hz), 1.219 (3H, d, J=6.8 Hz), 1.25–1.51 (4H, m), 1.65–1.74 (3H, m), 1.86–2.05 (1H, m), 2.58–2.70 (1H, m), 3.900 (1H, d, d→q, J=2 Hz, J=10 Hz)

$^1$H-NMR spectrum (400 MHz, C$_6$D$_6$): 0.456 (3H, d, J=6.8 Hz), 0.814 (3H, d, J=6.5 Hz), 0.870 (3H, t, J=7.2 Hz), 0.989 (1H, ddd, J=7 Hz, 8 Hz, 13.5 Hz), 1.068 (3H, d, J=7 Hz), 1.096–1.300 (3H, m), 1.318–1.443 (3H, m), 1.508 (1H, dddq, J=7.5 Hz, J=7.5 Hz, J=10 Hz, J=7 Hz), 2.040 (1H, ddq, J=8 Hz, J=9 Hz, J=7 Hz), 3.442 (1H, dd, J=0.8 Hz, J=10 Hz)

$^{13}$C-NMR spectrum (100 MHz, CDCl$_3$): 12.349, 14.154, 16.622, 17.697, 20.465, 28.436, 32.558, 33.693, 35.484, 36.140, 85.737, 176.682

Gas chromatography (Carbowax 20M, 0.2 mm×25 m, 120° C.→140° C., 3° C./min, He 0.7 ml/min): Rt 9.66 min (98.2%)

$[\alpha]_D^{27}$: −105° (c=0.29, CHCl$_3$)

Synthesis of (+)-invictolide (b)

(−)-invictolide (b) was produced by operating in the same way as above except that (−)-(Ib) was used instead of (+)-(Ib).

$[\alpha]_n^{22}$: +101° (c=0.615, CHCl$_3$)

| Elemental analysis ($C_{12}H_{22}O_2$): | | |
|---|---|---|
| | C | H |
| Found: | 72.51 | 11.15 |
| Calculated: | 72.68 | 11.18 |

While the invention has been described in detail and with reference to specific embodiments thereof, it will be apparent to one skilled in the art that various changes and modifications can be made therein without departing from the spirit and scope thereof.

What is claimed is:

1. An optically active alcohol represented by the structural formula wherein the configuration of the 2, 3 and 4 positions is (2R,3S,4R) or (2S,3R,4S).

2. An alcohol as claimed in claim 1, wherein the configuration of the 2-, 3- and 4-positions is (2R,3S,4R).

3. An alcohol as claimed in claim 1, wherein the configuration of the 2-, 3- and 4-positions is (2S,3R,4S).

* * * * *